US012678832B2

(12) United States Patent
Schneider et al.

(10) Patent No.: US 12,678,832 B2
(45) Date of Patent: Jul. 14, 2026

(54) MAGNETIC RESONANCE APPARATUS WITH CLEANING UNIT AND METHOD FOR CLEANING A PATIENT RECEIVING AREA

(71) Applicant: Siemens Healthcare GmbH, Erlangen (DE)

(72) Inventors: Michael Schneider, Erlangen (DE); Stefanie Gügel-Wild, Langensendelbach (DE); Bernd Maciejewski, Markt Bibart (DE); Marianne Köferl, Fichtelberg (DE); Annette Stein, Spardorf (DE)

(73) Assignee: Siemens Healthineers AG, Erlangen (DE)

( * ) Notice: Subject to any disclaimer, the term of this patent is extended or adjusted under 35 U.S.C. 154(b) by 366 days.

(21) Appl. No.: 17/669,916

(22) Filed: Feb. 11, 2022

(65) Prior Publication Data

US 2022/0258212 A1    Aug. 18, 2022

(30) Foreign Application Priority Data

Feb. 15, 2021    (EP) ..................................... 21157162

(51) Int. Cl.
| | |
|---|---|
| *B08B 13/00* | (2006.01) |
| *A61B 5/00* | (2006.01) |
| *A61B 5/055* | (2006.01) |
| *B08B 3/02* | (2006.01) |

(Continued)

(52) U.S. Cl.
CPC ............. *B08B 3/024* (2013.01); *A61B 5/055* (2013.01); *A61B 5/704* (2013.01); *B08B 3/08* (2013.01); *G01R 33/385* (2013.01)

(58) Field of Classification Search
None
See application file for complete search history.

(56) References Cited

U.S. PATENT DOCUMENTS

| | | | | |
|---|---|---|---|---|
| 9,194,920 | B2 * | 11/2015 | Hu | ....................... G01R 33/307 |
| 2012/0136196 | A1 | 5/2012 | Foxall et al. | |

(Continued)

FOREIGN PATENT DOCUMENTS

| | | | |
|---|---|---|---|
| CN | 204931704 U | 1/2016 | |
| CN | 107457225 B * | 6/2020 | ............... A61L 2/10 |
| CN | 112043844 A | 12/2020 | |

OTHER PUBLICATIONS

Google Patents translation of CN112043844A retrieved from https://patents.google.com/patent/CN112043844A/en?oq=cn+112043844 on Jun. 27, 2023 (Year: 2023).*

(Continued)

*Primary Examiner* — Eric W Golightly
(74) *Attorney, Agent, or Firm* — Banner & Witcoff, Ltd.

(57) ABSTRACT

The present disclosure is directed a magnetic resonance apparatus with a scanner unit, a patient receiving area at least partially surrounded by the scanner unit, wherein the scanner unit includes an enclosure at least partially surrounding the patient receiving area, and a patient support apparatus with a patient table, wherein the patient table is embodied to move horizontally within the patient receiving area, wherein the magnetic resonance apparatus comprises a cleaning unit for cleaning the enclosure surrounding the patient receiving area, wherein the cleaning unit is at least partially arranged on the patient table.

17 Claims, 6 Drawing Sheets

Figure 1:
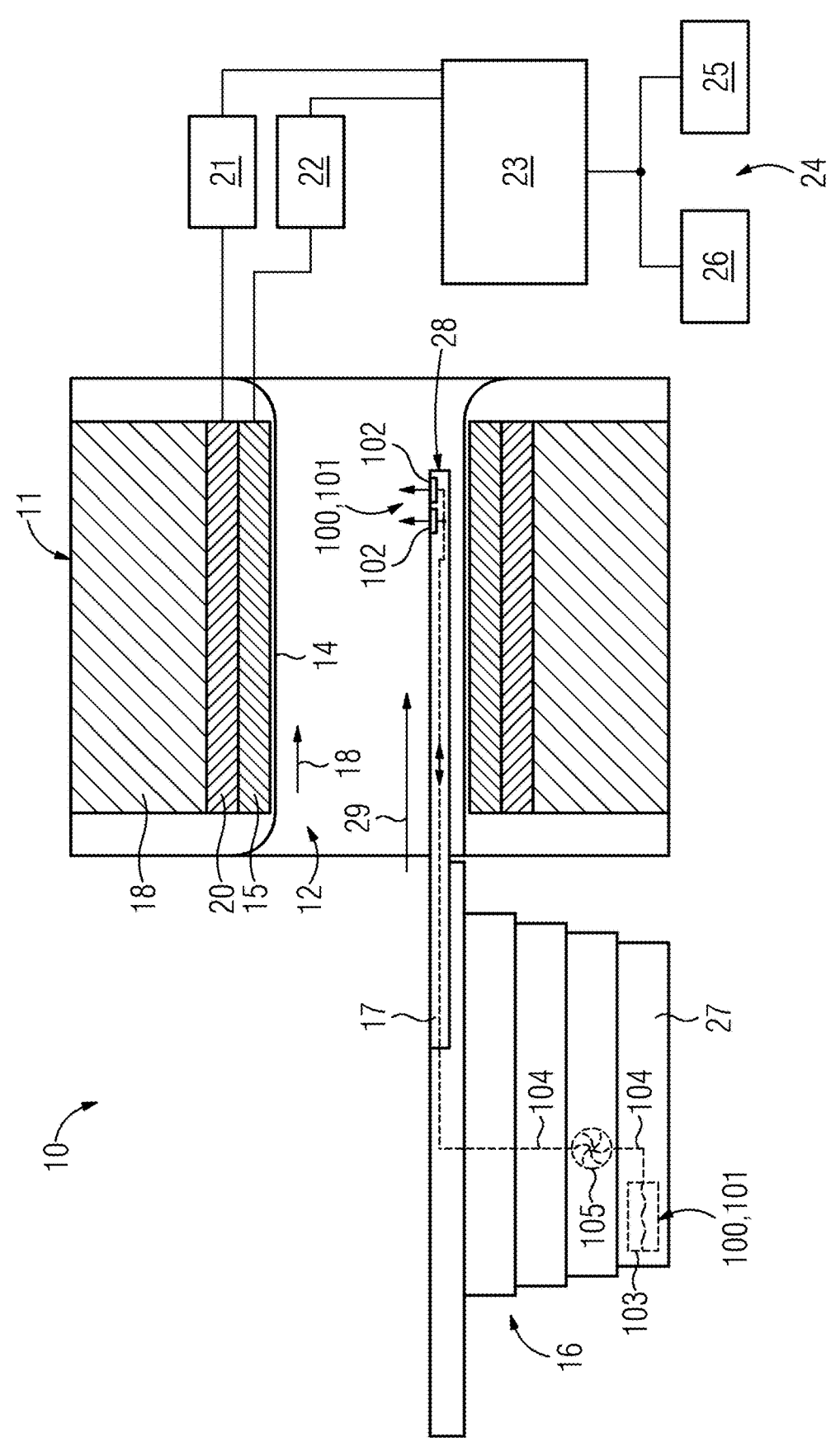

(51) Int. Cl.
    *B08B 3/08*           (2006.01)
    *G01R 33/385*     (2006.01)

(56)                 References Cited

U.S. PATENT DOCUMENTS

| | | | |
|---|---|---|---|
| 2019/0262876 A1* | 8/2019 | Werner | B08B 15/026 |
| 2020/0001024 A1* | 1/2020 | Chen | A61M 15/0001 |

OTHER PUBLICATIONS

CN107457225B translation (Year: 2023).*
Butler, Norman et al: "Device for MRI scanner intra-bore disinfection"; Penn Center for Innovation, Empowering Ideas, Penn Center for Innovation, US; Jun. 23, 2020 (Jun. 23, 2020); p. 1; XP009528630.

* cited by examiner

MAGNETIC RESONANCE APPARATUS WITH CLEANING UNIT AND METHOD FOR CLEANING A PATIENT RECEIVING AREA

CROSS-REFERENCE TO RELATED APPLICATIONS

The present application claims the benefit of the filing date of European patent application no. EP21157162.5, filed on Feb. 15, 2021, the contents of which are incorporated herein by reference in their entirety.

TECHNICAL FIELD

The disclosure relates to a magnetic resonance apparatus with a scanner unit, a patient receiving area at least partially surrounded by the scanner unit, wherein the scanner unit includes an enclosure at least partially surrounding the patient receiving area, and a patient support apparatus with a patient table, wherein the patient table is embodied to move horizontally within the patient table. In addition, the present disclosure also relates to a method for cleaning a patient receiving area, e.g. an enclosure surrounding the patient receiving area, of a magnetic resonance apparatus by means of a cleaning unit.

BACKGROUND

During magnetic resonance examinations in which the patient is introduced and/or moved head first into a patient receiving area, the patient's head is located within the patient receiving area for the entire duration of the magnetic resonance examination. As the patient receiving area is embodied with a diameter of approximately 60 cm to 80 cm and a length of 1.2 m to 1.8 m, during this period the head of the patient is located relatively close to an enclosure of the magnetic resonance apparatus surrounding the patient receiving area. This means that the patient's breathing and/or coughing etc. can result in soiling and/or contamination of the patient receiving area and/or also of the patient table.

There are different methods for cleaning the patient table and the enclosure surrounding the patient receiving area. Although, when it has been moved out of the patient receiving area, the patient table is freely accessible to cleaning staff and is thus easy to clean, it is particularly difficult to clean the patient receiving area, e.g. the enclosure surrounding the patient receiving area, due to the length of the patient receiving area. With lengths of the magnetic resonance apparatus, and hence also of the patient receiving area, of 1.5 m and more, it is very difficult for cleaning staff to reach the soiled areas and/or contaminated areas within the patient receiving area, in particular within the enclosure surrounding the patient receiving area.

SUMMARY

The object underlying the present disclosure is to enable simple and time-saving cleaning of the patient receiving area of a magnetic resonance apparatus. The object is achieved by the features as described in the embodiments discussed herein and in the claims.

The disclosure is based on a magnetic resonance apparatus with a scanner unit, a patient receiving area at least partially surrounded by the scanner unit, wherein the scanner unit includes an enclosure at least partially surrounding the patient receiving area, and a patient support apparatus with a patient table, wherein the patient table is embodied (i.e. configured to) to move horizontally within the patient receiving area. According to the disclosure, the magnetic resonance apparatus comprises a cleaning unit for cleaning the enclosure surrounding the patient receiving area, wherein the cleaning unit is at least partially arranged on the patient table.

The magnetic resonance apparatus may include a medical and/or diagnostic magnetic resonance apparatus, designed and/or embodied to acquire medical and/or diagnostic image data, e.g. medical and/or diagnostic magnetic resonance image data, from a patient. For this purpose, the magnetic resonance apparatus includes the scanner unit. The scanner unit of the magnetic resonance apparatus may include a detector unit, e.g. a magnet unit, for acquiring the medical and/or diagnostic image data. In this case, the scanner unit, e.g. the magnet unit, may include a main magnet, a gradient system, and a radio-frequency antenna unit. The radio-frequency antenna unit is fixed within the scanner unit and is designed and/or embodied to emit an excitation pulse. To acquire the magnetic resonance signals, the magnetic resonance apparatus comprises local radio-frequency antenna units arranged around the area of the patient to be examined.

The main magnet is embodied to generate a homogeneous main magnetic field with a defined and/or specific magnetic field strength, such as, for example, with a defined and/or specific magnetic field strength of 3 T or 1.5 T etc. The main magnet may be embodied to generate a strong, constant, and homogeneous main magnetic field. The homogeneous main magnetic field may be arranged and/or to be found within a patient receiving area of the magnetic resonance apparatus. The gradient system is embodied to generate magnetic field gradients used for spatial encoding during imaging.

The patient receiving area is designed and/or embodied to receive the patient, e.g. the area of the patient to be examined, for a medical magnetic resonance examination. For example, for this purpose, the patient receiving area is embodied with a cylindrical shape and/or is surrounded by the scanner unit in the shape of a cylinder. For this purpose, the scanner unit comprises an enclosure at least partially surrounding the patient receiving area. The enclosure of the scanner unit preferably surrounds the patient receiving area in a cylindrical shape. In this case, the enclosure can also include a side of the radio-frequency antenna unit facing the patient receiving area and/or be embodied in one piece with the side of the radio-frequency antenna unit facing the patient receiving area.

A field of view (FOV) and/or an isocenter of the magnetic resonance apparatus is arranged within the patient receiving area. The FOV may include an acquisition area of the magnetic resonance apparatus within which conditions exist for the acquisition of medical image data, e.g. magnetic resonance image data, within the patient receiving area, such as, for example, a homogeneous main magnetic field. The isocenter of the magnetic resonance apparatus may include the area and/or point within the magnetic resonance apparatus comprising optimal and/or ideal conditions for the acquisition of medical image data, e.g. magnetic resonance image data. The isocenter may include the most homogeneous magnetic field region within the magnetic resonance apparatus.

For positioning the patient, e.g. the area of the patient to be examined, within the patient receiving area the magnetic resonance apparatus comprises the patient support apparatus. The patient support apparatus may comprise the movable patient table. The patient table is embodied to support the patient. For a magnetic resonance examination, the patient is first positioned on the patient table of the patient support apparatus and then the patient table is positioned together with the patient within the patient receiving area until the area of the patient to be examined is arranged within the FOV and/or the isocenter of the magnetic resonance apparatus, e.g. the scanner unit. In this case, the patient table is embodied and/or supported so it can be moved in the horizontal direction, e.g. in the direction of insertion, into the patient receiving area.

The cleaning unit may be embodied to clean the patient receiving area, e.g. the enclosure surrounding the patient receiving area. The cleaning unit is at least partially arranged on the patient table so that a cleaning operation can be started and/or performed during a horizontal movement of the patient table. In this case, after a magnetic resonance examination on a patient, the patient table may be moved into the patient receiving area for cleaning the patient receiving area, e.g. the enclosure surrounding the patient receiving area. The cleaning unit may comprise a plurality of modules and/or units, wherein at least one of these units and/or modules are arranged on the patient table.

In this regard, the cleaning unit can be embodied in such a way that the cleaning operation can be carried out at least partially automatically and/or autonomously by the cleaning unit, e.g. after a magnetic resonance examination has been completed. In this case, the cleaning unit may comprise a control unit and/or a computing unit embodied to control the execution of the cleaning operation by means of the cleaning unit.

The disclosure enables simple and time-saving cleaning of the enclosure of the magnetic resonance apparatus surrounding the patient receiving area. For instance, the at least partial arrangement of the cleaning unit on the patient table can enable good accessibility of soiled and/or contaminated areas within the patient receiving area, and hence efficient cleaning of the enclosure surrounding the patient receiving area, to be achieved. In this case, a cleaning operation may be performed by means of the cleaning unit during a horizontal movement of the patient table, e.g. a movement of the patient table into the patient receiving area and/or a movement of the patient table out of the patient receiving area.

In an advantageous development of the magnetic resonance apparatus according to the disclosure, it can be provided that the cleaning unit comprises at least one unit, which is arranged within the patient table and/or can be arranged and/or positioned on the patient table as an additional unit. In this case, a unit, which is arranged within the patient table, should e.g. be understood to be a unit of the cleaning unit arranged in an area enclosed by a housing of the patient table. In this case, an additional unit that can be arranged and/or positioned on the patient table should e.g. be understood to mean that the additional unit is only arranged and/or positioned on the patient table for cleaning purposes and is dismantled and/or removed from the patient table during a magnetic resonance examination on a patient. This enables a particularly space-saving arrangement of the cleaning unit to be provided. In addition, this can also advantageously prevent impairment of a support surface of the patient table for supporting the patient. For instance, such an arrangement of the cleaning unit on the patient table can advantageously prevent any restriction of the space and/or area available within the patient receiving area for a patient during a magnetic resonance examination. In addition, the embodiment of the cleaning unit as an additional unit, which can be arranged and/or positioned on the patient table for cleaning the enclosure surrounding the patient receiving area enables magnetic resonance apparatus systems and/or patient support apparatus systems that already exist and/or are already in use to be retrofitted with a cleaning unit in a particularly simple manner. This also enables cleaning of the enclosure surrounding the patient receiving area to be achieved or provided in a structurally simple manner.

In an advantageous development of the magnetic resonance apparatus according to the disclosure, it can be provided that the cleaning unit comprises a spray unit, wherein the spray unit comprises nozzles for distributing a cleaning agent. The cleaning agent may include a cleaning fluid so that the distribution of the cleaning agent includes spraying the cleaning fluid. The spray unit, e.g. the nozzles of the spray unit, is may be arranged on the patient table in such a way that, during the distribution of the cleaning agent, the cleaning agent lands on the enclosure of the patient receiving area. In this case, the nozzles of the spray unit are may be integrated in the patient table and/or arranged thereupon as an additional unit. In this regard, the nozzles can be directed upward, e.g. toward a side of the enclosure of the patient receiving area facing a support surface of the patient table, so that an area of the enclosure of the patient receiving area that is exposed to a high probability of contamination and/or soiling during a magnetic resonance examination, for example due to breathing and/or coughing of the patient, is included in the distribution of the cleaning agent, e.g. the spraying of the cleaning fluid. This embodiment of the disclosure enables a simple and efficient, in particular wide-area, distribution of a cleaning agent, e.g. a cleaning fluid, within the patient receiving area, e.g. onto an enclosure surrounding the patient receiving area.

In an advantageous development of the magnetic resonance apparatus according to the disclosure, it can be provided that the nozzles are arranged in a front area of the patient table. The front area of the patient table may include an area, which, when the patient table is moved into the patient receiving area, is arranged at an end of the patient table facing in the direction of travel, and/or which first enters the patient receiving area when the patient table is moved into the patient receiving area. In this regard, the spray unit with the nozzles can be integrated in the front area of the patient table or can also be arranged and/or positioned as an additional unit in the front area of the patient table.

Such an embodiment of the disclosure enables good distribution of a cleaning agent, e.g. a cleaning fluid, within the patient receiving area, e.g. on the enclosure surrounding the patient receiving area, over the entire length of the patient receiving area. The arrangement of the nozzles in the front area of the patient table may enable the movement of the patient table into the patient receiving area to be commenced at the same time as the dispensing and/or spraying of the cleaning agent, e.g. the cleaning fluid. In addition, this also enables the patient receiving area, e.g. the enclosure surrounding the patient receiving area, to be cleaned along its entire length, e.g. from an insertion opening of the patient receiving area to the position of the front end of the patient table, which comprises the front end of the patient table when the insertion movement of the patient table is completed.

In an advantageous development of the magnetic resonance apparatus according to the disclosure, it can be provided that the spray unit comprises a storage tank arranged on a base unit of the patient support apparatus. In this context, a base unit of the patient support apparatus should be understood to be a unit that does not perform any movement relative to the magnetic resonance apparatus and/or relative to the patient receiving area during a horizontal movement of the patient table into or out of the patient receiving area. The base unit of the patient support apparatus may also be embodied to support and/or bear the patient table when the patient table is located outside the patient receiving area. The storage tank may be embodied to receive a cleaning agent. The storage tank is e.g. embodied as a fluid tank for receiving a cleaning fluid. Herein, the storage tank, e.g. the fluid tank, can be embodied to be refillable or also as a replaceable and/or exchangeable single-use tank. In this regard, the arrangement of the storage tank, e.g. the fluid tank, within the base unit of the patient support apparatus can include an arrangement within an area surrounded by a housing of the base unit, such as, for example, a receiving compartment for receiving the fluid tank. Alternatively or additionally, the storage tank, e.g. the fluid tank, can also be arranged on an outer side of the base unit of the patient support apparatus, such as, for example, an arrangement by means of a retaining element and/or a fastening element on the base unit. The storage tank, e.g. the fluid tank, may be arranged on the base unit in a manner accessible to users and/or cleaning staff.

Such an embodiment of the disclosure has the advantage that a sufficiently large supply of cleaning agent, e.g. cleaning fluid, is available for cleaning the enclosure surrounding the patient receiving area and that the cleaning of the enclosure surrounding the patient receiving area can be performed without interruption. In addition, the spray unit can also comprise more than one storage tank, e.g. more than one fluid tank, wherein the two or more reservoirs contain different cleaning agents for cleaning the enclosure surrounding the patient receiving area in different cleaning stages.

Alternatively, when the cleaning unit, e.g. the spray unit, is embodied as an additional unit that can be attached to and/or removed from the patient table, the storage tank for receiving the cleaning agent can also be embodied as an additional unit. In this regard, for a cleaning operation on the enclosure surrounding the patient receiving area, the storage tank embodied as an additional unit can also be arranged and/or positioned on the patient table. In addition, it is also possible that, for a cleaning operation on the enclosure surrounding the patient receiving area, the storage tank embodied as an additional unit can also be arranged and/or positioned on the base unit, such as, for example, by means of fastening means and/or holding means, and/or positioned at other locations which the person skilled in the art considers to be advisable during cleaning of the enclosure surrounding the patient receiving area.

In addition, the spray unit can comprise further units, such as, for example, a pump and/or a cleaning agent duct, etc. The storage tank, e.g. the fluid tank, may be connected to the nozzles of the spray unit by means of the cleaning agent duct, so that the cleaning agent can be fed from the storage tank, e.g. the fluid tank, to the nozzles. The cleaning agent, e.g. the cleaning fluid, may be pumped from the storage tank to the nozzles by means of the pump. In addition, the spray unit and/or the cleaning unit can also include a control unit that controls the distribution and/or dispensing of the cleaning agent, e.g. the spraying of the cleaning fluid, by means of the spray unit.

In an advantageous development of the magnetic resonance apparatus according to the disclosure, it can be provided that the cleaning unit comprises a drying unit, wherein the drying unit is embodied to allow drying air to flow into the patient receiving area. For this purpose, the drying unit may include air inlet openings which open into the patient receiving area. These air inlet openings can, for example, include nozzles through which the drying air is able to flow into the patient receiving area. These nozzles can be specially embodied to allow the inflow of air, e.g. drying air. In addition, these nozzles of the drying unit can also be at least partially embodied in one piece and/or one part with the nozzles of the suction unit, thus enabling a particularly compact cleaning unit for cleaning the patient receiving area, e.g. the enclosure surrounding the patient receiving area, to be achieved. Furthermore, the drying unit comprises a fan and/or ventilator for generating an air flow and an air supply duct for transporting the drying air.

This embodiment of the disclosure has the advantage that rapid drying of the patient receiving area, e.g. the enclosure surrounding the patient receiving area, is provided after a cleaning operation, hence enabling the prevention of a long waiting time until the magnetic resonance apparatus is again available for a magnetic resonance examination. As a result, despite the fact that the patient receiving area is cleaned after each magnetic resonance examination and/or after each change of patient, it is possible to achieve a high number of magnetic resonance examinations and hence high utilization of the magnetic resonance apparatus.

In an advantageous development of the magnetic resonance apparatus according to the disclosure, it can be provided that the drying unit is arranged at least partially on the patient table and/or on the enclosure surrounding the patient receiving area. If the drying unit is arranged on the patient table, the drying unit can be at least partially integrated within the patient table. In addition, in this case, the drying unit can also be positioned on the patient table as an additional unit for cleaning the patient receiving area. In this way, it is in particular possible for a cleaning operation of the enclosure surrounding the patient receiving area to be optimized in that, for example, when the patient table is moved into the patient receiving area, the cleaning agent, e.g. the cleaning fluid, is distributed onto the enclosure of the patient receiving area by means of the spray unit, e.g. the nozzles of the spray unit, and, when the patient table is moved out of the patient receiving area, the drying unit effects drying of the enclosure surrounding the patient receiving area.

Alternatively or additionally, the drying unit can also be at least partially arranged on the enclosure surrounding the patient receiving area. In this regard, the drying unit can, for example, be integrated within a patient ventilation system embodied to ventilate the patient receiving area. In this way, it is possible for a particularly compact and space-saving cleaning unit to be provided.

In an advantageous development of the magnetic resonance apparatus according to the disclosure, it can be provided that the cleaning unit comprises a suction extraction unit. A suction extraction unit advantageously enables a MAC value (maximum allowable workplace concentration value) of cleaning agent aerosols in the air to be maintained within a permissible range after the application of the cleaning agent, e.g. the spraying of the cleaning agent, and thereby also enables any risk and/or impairment to the patient's health to be reduced during a magnetic resonance examination following the cleaning of the enclosure surrounding the patient receiving area.

The suction extraction unit may include a ventilator and/or a fan and/or a suction extraction pump embodied to generate a suction flow. In addition, the suction extraction unit preferably comprises at least one suction extraction opening, which can, for example, also include a suction extraction nozzle. In addition, the suction extraction unit can also include a suction extraction duct, which transports aspirated air further, e.g. transports it away from the patient receiving area.

In an advantageous development of the magnetic resonance apparatus according to the disclosure, it can be provided that the suction extraction unit is at least partially arranged on the enclosure surrounding the patient receiving area and/or on the patient table. The suction extraction unit may comprise at least one suction extraction opening and/or at least one suction nozzle, wherein the at least one suction extraction opening and/or the at least one suction nozzle is arranged on the enclosure surrounding the patient receiving area and/or on the patient table. In this regard, the at least one suction extraction opening and/or the at least one suction nozzle of the suction extraction unit can be at least partially integrated within the patient table. In addition, the suction extraction unit, e.g. the at least one suction extraction opening and/or the at least one suction nozzle of the suction extraction unit, can also be at least partially embodied in one piece and/or one part with the spray unit. For example, in this case, the nozzles of the spray unit can be embodied as a double nozzle that is both able to apply and/or spray a cleaning agent and is embodied for the extraction of cleaning aerosols by suction after the application of cleaning agent.

In addition, the suction extraction unit can also be arranged and/or positioned as an additional unit on the patient table for cleaning the enclosure surrounding the patient receiving area. In this regard, the suction extraction unit can be arranged in the direction of insertion of the patient table, for example downstream of the spray unit, e.g. in a central area of the patient table and/or in a rear area of the patient table. In addition, the suction extraction unit can also comprise a suction extraction opening which is arranged on the enclosure of the patient receiving area and is thus able to extract the air from the patient receiving area by suction. In this regard, the suction extraction unit can comprise one or more suction extraction openings and/or suction nozzles.

This embodiment of the disclosure can achieve the advantage that a particularly space-saving arrangement of the suction extraction unit can be provided.

In an advantageous development of the magnetic resonance apparatus according to the disclosure, it can be provided that the suction extraction unit includes at least one suction extraction duct with a filter. In this way, it is not only possible for the air to be extracted from the patient receiving area by suction; it can also be cleaned with respect to cleaning aerosols. In addition, this is a particularly efficient way of maintaining a MAC value for the cleaning agent. The ventilation duct may also comprise an outlet opening, wherein the filter is arranged in the direction of flow of aspirated air upstream of the outlet opening. The filter may be arranged exchangeably within the suction extraction duct, wherein, for this purpose, the filter is arranged in the vicinity of the outlet opening in order to thus enable easy accessibility for users, for example cleaning staff, in order to change the filter.

In addition, the disclosure is based on a method for cleaning a patient receiving area, e.g. an enclosure surrounding the patient receiving area, of a magnetic resonance apparatus by means of a cleaning unit, wherein the method includes the following steps:

moving a patient table into the patient receiving area, wherein the cleaning unit is arranged on the patient table, at the same time as the patient table is moved into the patient receiving area, a first cleaning step of a cleaning operation is executed, wherein the first cleaning step includes dispensing a cleaning agent by means of the cleaning unit, and executing a second cleaning step, wherein the second cleaning step includes a drying step and/or a suction extraction step.

The dispensing of the cleaning agent may include the distribution, e.g. spraying, of a cleaning fluid by means of a spray unit of the cleaning unit. The spray unit may comprise at least one nozzle, which can be integrated within the patient table. In addition, the spray unit can also be arranged and/or positioned on the patient table as an additional unit for a cleaning operation. The spray unit, e.g. the at least one nozzle of the spray unit, may be arranged and/or positioned in a front area of the patient table.

The arrangement and/or positioning of the cleaning unit, e.g. the spray unit, in the front area of the patient table means the spray unit is already located within the patient receiving area when the patient table starts to be moved into the patient receiving area. Therefore, the dispensing of the cleaning agent, e.g. spraying of the cleaning fluid, by means of the spray unit can be commenced at the same time as the patient table is moved into the patient receiving area. This means that the patient receiving area, e.g. the enclosure surrounding the patient receiving area, can also be sprayed with a cleaning agent along its entire length and hence cleaned.

The second cleaning step of the cleaning operation includes the drying step and/or the suction extraction step. Both the drying step and the suction extraction step are executed by means of the cleaning unit. For this purpose, the cleaning unit may comprise a drying unit and/or a suction extraction unit. The drying unit can be used to blow a drying air into the patient receiving area, which causes rapid drying of the surface of the patient receiving area, e.g. the surface of the enclosure of the patient receiving area. The suction extraction unit can be used to extract cleaning agent aerosols by suction and hence to keep the concentration of cleaning agent aerosols low, e.g. to maintain a MAC value for cleaning agent aerosols. In this case, the drying unit and/or the suction extraction unit may be arranged on the patient table and/or arranged on the enclosure surrounding the patient receiving area. In this regard, if the drying unit and/or the suction extraction unit are arranged on the patient table, the drying unit and/or the suction extraction unit can be at least partially integrated in the patient table. Alternatively, it is also possible for the drying unit and/or the suction extraction unit to be arranged and/or positioned on the patient table as an additional unit for a cleaning operation for cleaning the enclosure surrounding the patient receiving area.

The method according to the disclosure for cleaning the patient receiving area, e.g. the enclosure surrounding the patient receiving area, enables simple and efficient cleaning of the enclosure of the magnetic resonance apparatus surrounding the patient receiving area. In this case, the cleaning operation can e.g. be performed by means of the cleaning unit during a single insertion and removal of the patient table, hence enabling particularly time-saving cleaning of the enclosure surrounding the patient receiving area.

The advantages of the method according to the disclosure for cleaning an enclosure surrounding the patient receiving area substantially correspond to the advantages of the magnetic resonance apparatus according to the disclosure as described above in detail. Features, advantages or alternative embodiments mentioned in this case can likewise be transferred to the other claimed subject matter and vice versa.

In an advantageous development of the method according to the disclosure for cleaning a patient receiving area, it can be provided that the second cleaning step is executed while the patient table is moved into the patient receiving area and/or while the patient table is moved out of the patient receiving area. In this regard, the second cleaning step can be executed the first time the patient table is moved into the patient receiving area during which time the first cleaning step is also executed. Alternatively or additionally, the second cleaning step can also be executed while the patient table is moved out of the patient receiving area, so that the patient table only has to be moved into and out of the patient receiving area once in order to clean the patient receiving area. This can enable particularly rapid and time-saving cleaning of the patient receiving area.

BRIEF DESCRIPTION OF THE DRAWINGS/FIGURES

Figure 2:
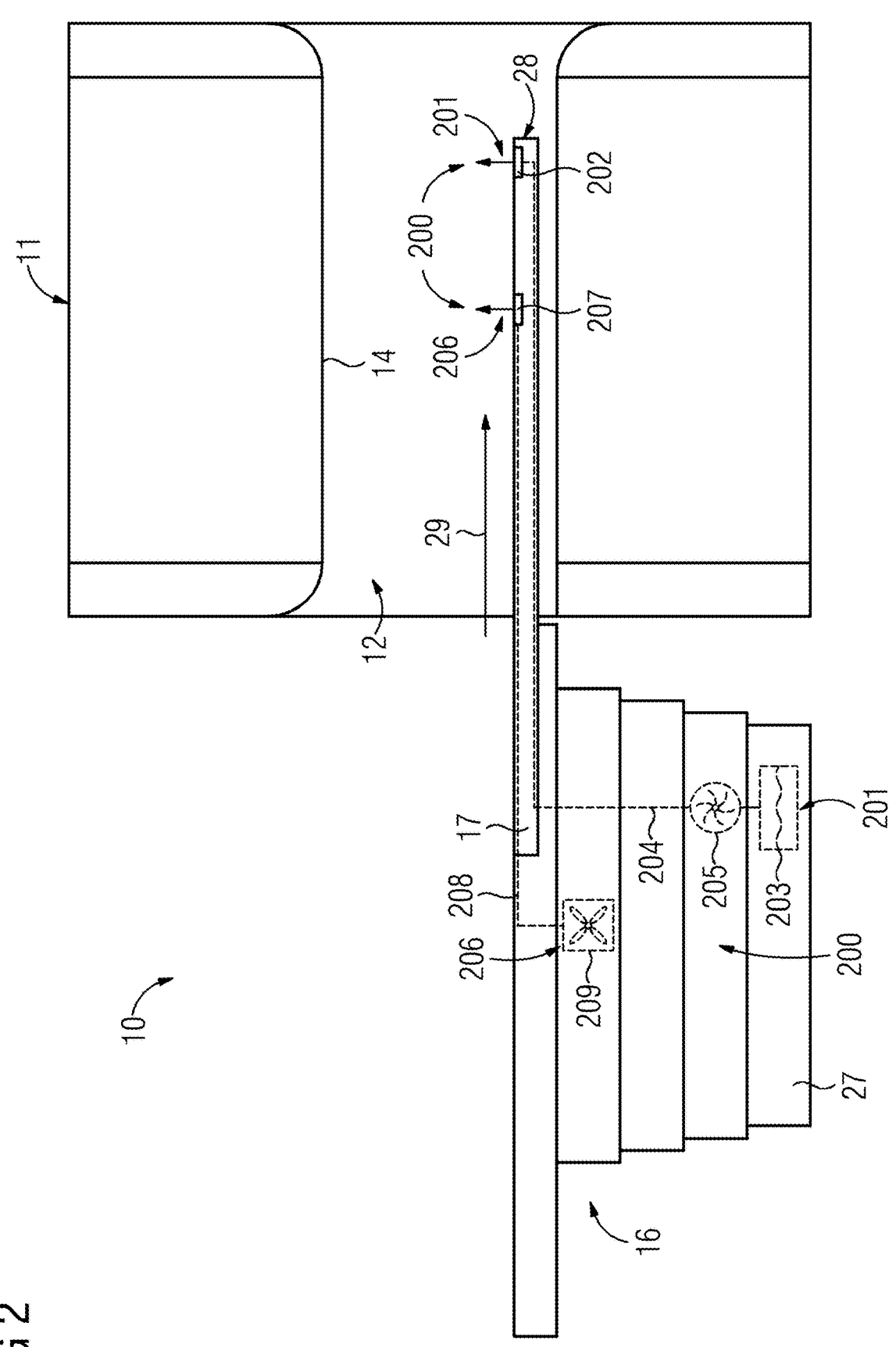
Figure 3:
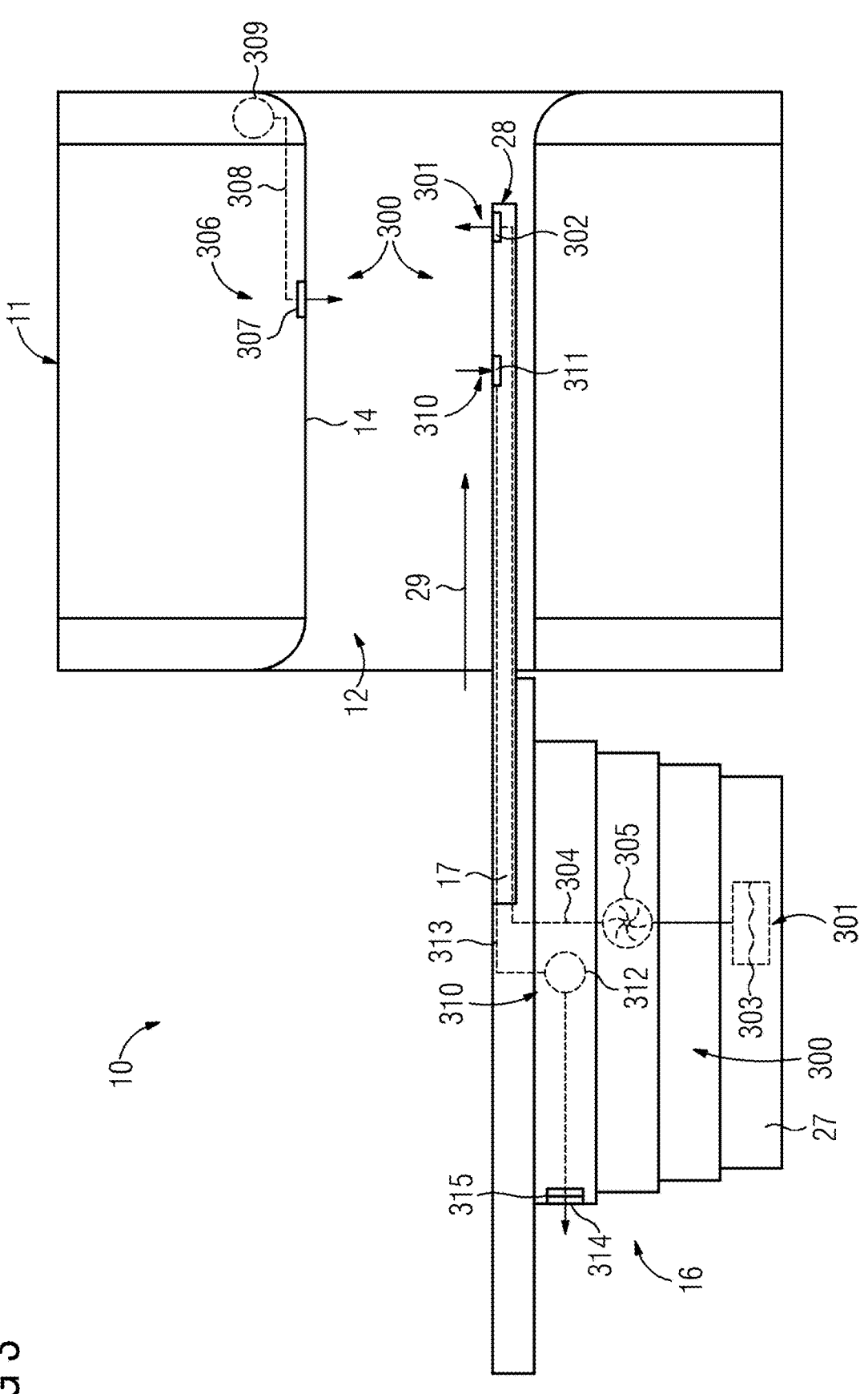
Figure 4:
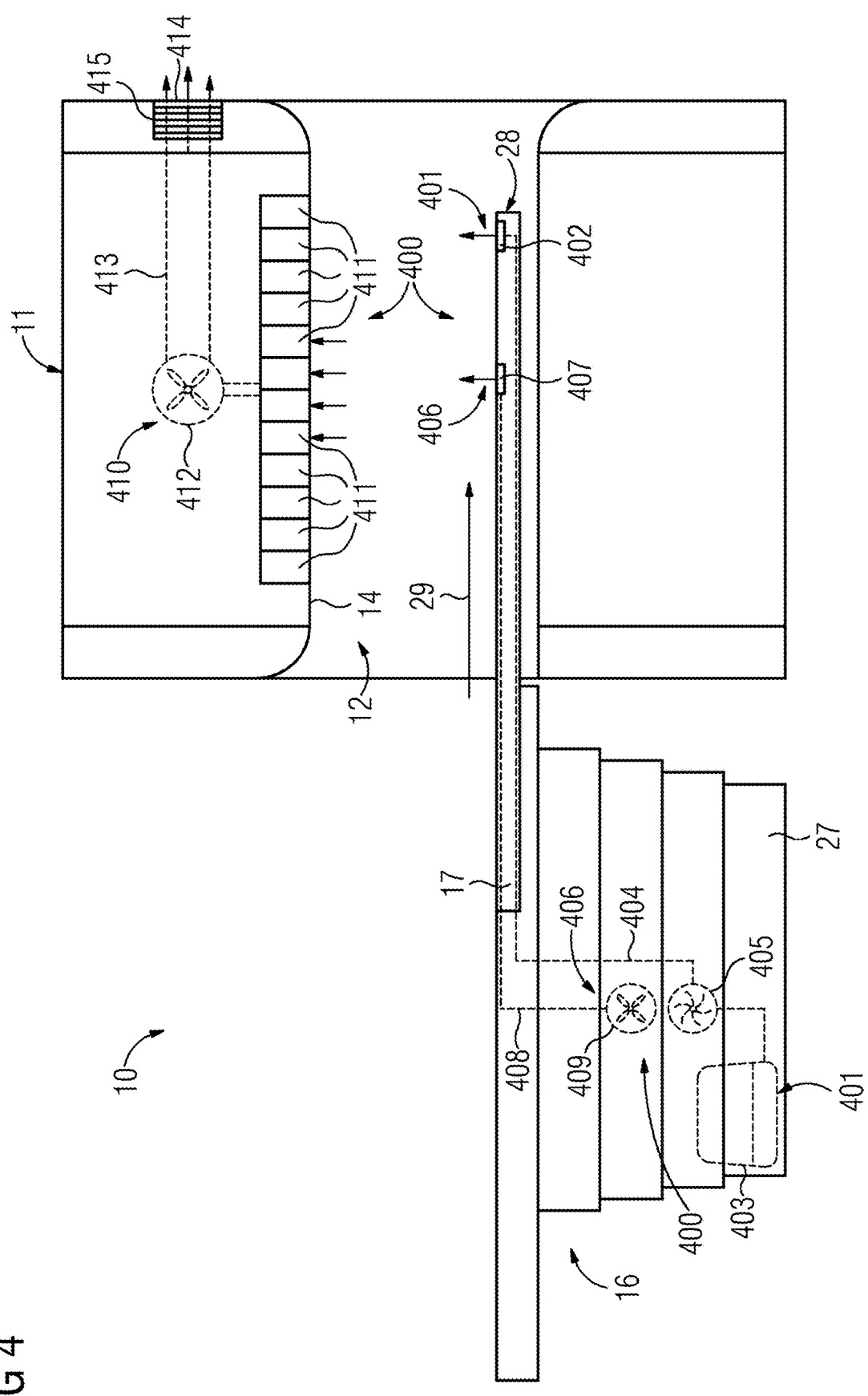
Figure 5:
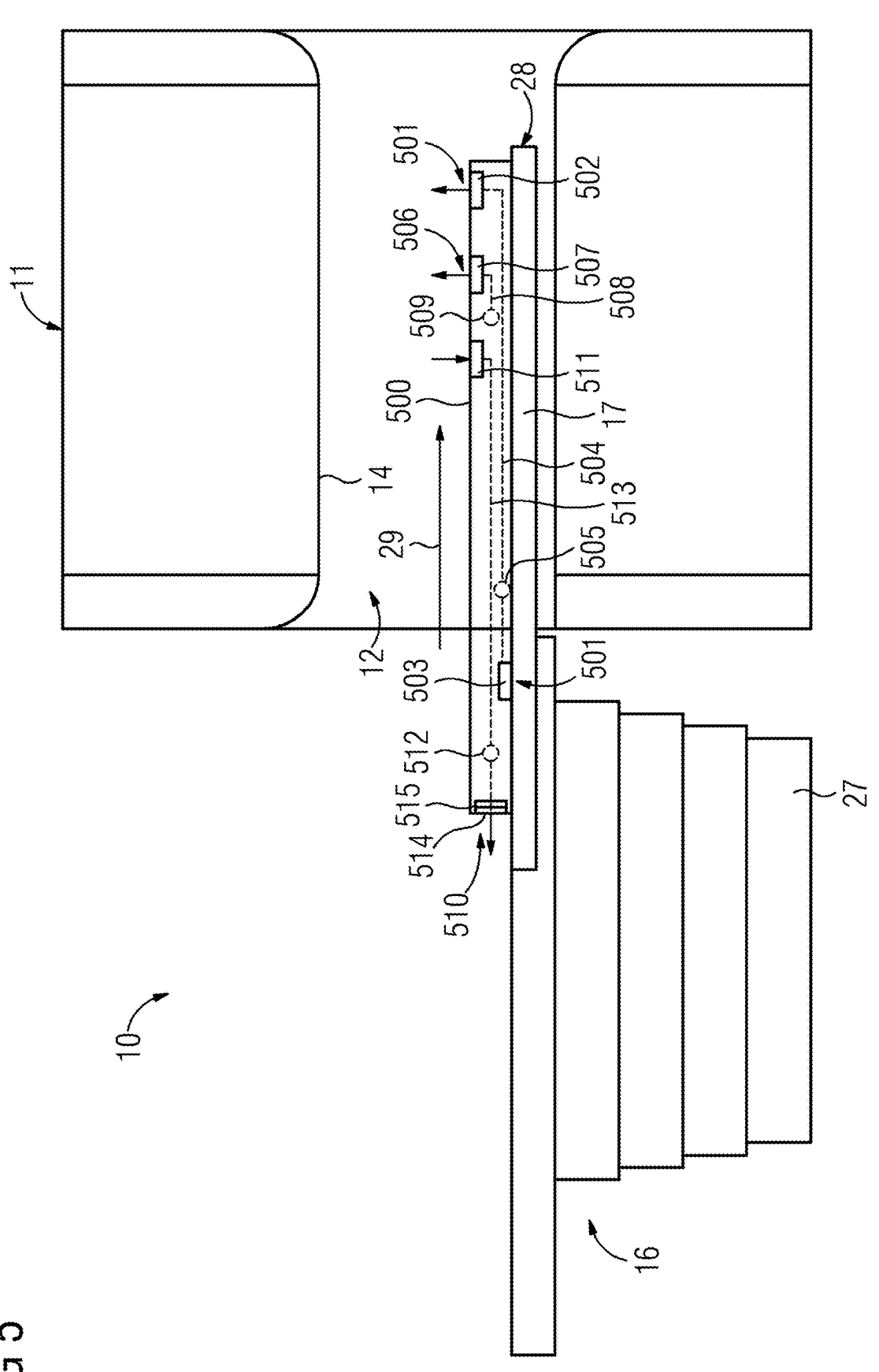
Figure 6:
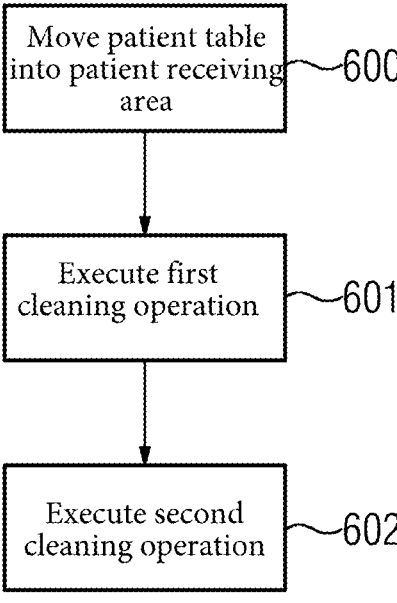

Further advantages, features and details of the disclosure will emerge from the exemplary embodiments described in the following and with reference to the drawings:

FIG. 1 illustrates a magnetic resonance apparatus according to the disclosure with a cleaning unit in a schematic representation, FIG. 2 illustrates a representation of the magnetic resonance apparatus with an alternative embodiment of a cleaning unit, FIG. 3 illustrates a representation of the magnetic resonance apparatus with a further alternative embodiment of a cleaning unit, FIG. 4 illustrates a representation of the magnetic resonance apparatus with a further alternative embodiment of a cleaning unit, FIG. 5 illustrates a representation of the magnetic resonance apparatus with a further alternative embodiment of a cleaning unit; and FIG. 6 illustrates a method according to the disclosure for cleaning a patient receiving area of a magnetic resonance apparatus.

DETAILED DESCRIPTION

FIG. 1 illustrates a schematic representation of a magnetic resonance apparatus (or imager) 10. The magnetic resonance apparatus 10 includes a scanner unit (or scanner) 11 formed by a magnet unit. In addition, the magnetic resonance apparatus 10 comprises a patient receiving area 12 for receiving a patient. In the present exemplary embodiment, the patient receiving area 12 is cylindrical in shape and is surrounded in a circumferential direction by the scanner unit 11, e.g. by the magnet unit, in a cylindrical shape. However, in principle any suitable embodiment and/or shape of the patient receiving area 12 is conceivable.

In this regard, the scanner unit 11 comprises an enclosure 14 surrounding the patient receiving area 12. In this regard, the enclosure 14 surrounding the patient receiving area 12 can be embodied in one piece with a radio-frequency antenna unit 15 of the scanner unit 11, e.g. the magnet unit. In addition, the enclosure 14 surrounding the patient receiving area 12 can also be embodied separately from the radio-frequency antenna unit 15.

The patient can be pushed and/or moved into the patient receiving area 12 by means of a patient support apparatus (or patient support) 16 of the magnetic resonance apparatus 10.

For this purpose, the patient support apparatus 16 comprises a patient table 17 embodied movably within the patient receiving area 12. In this case, the patient table 17 is in particular supported so as to be movable in the direction of a longitudinal extension of the patient receiving area 12 and/or in the horizontal direction.

The scanner unit 11, e.g. the magnet unit, includes a superconducting main magnet 18 for generating a strong and in particular constant main magnetic field 19. Furthermore, the scanner unit 11, e.g. the magnet unit, comprises a gradient coil unit 20 for generating magnetic field gradients used for spatial encoding during imaging. The gradient coil unit 20 is controlled by means of a gradient control unit 21 of the magnetic resonance apparatus 10. The scanner unit 11, e.g. the magnet unit, further includes the radio-frequency antenna unit 15 for exciting polarization established in the main magnetic field 19 generated by the main magnet 18. The radio-frequency antenna unit 15 is controlled by a radio-frequency antenna control unit 22 of the magnetic resonance apparatus 10 and radiates radio-frequency magnetic resonance sequences into the patient receiving area 12 of the magnetic resonance apparatus 10.

To control the main magnet 18, the gradient control unit 21, and to control the radio-frequency antenna control unit 22, the magnetic resonance apparatus 10 comprises a system control unit 23. The system control unit 23 controls the magnetic resonance apparatus centrally, such as, for example, performing a predetermined imaging gradient echo sequence. In addition, the system control unit 23 includes an evaluation unit (not shown in further detail) for evaluating medical image data acquired during the magnetic resonance examination.

In addition, the magnetic resonance apparatus 10 includes a user interface 24 connected to the system control unit 23. Control information, such as, for example, imaging parameters, and reconstructed magnetic resonance images can be displayed on a display unit 25, for example on at least one monitor, of the user interface 24 for a medical operator. Furthermore, the user interface 24 comprises an input unit 26 by means of which information and/or parameters can be input by the medical operator during a scanning process.

For cleaning the patient receiving area 12, e.g. the enclosure 14 surrounding the patient receiving area 12 of the scanner unit 11, the magnetic resonance apparatus 10 comprises a cleaning unit 100 (also referred to as a cleaner or cleaning system). The cleaning unit 100 is at least partially arranged on the patient table 17 of the patient support apparatus 16. In this case, individual parts and/or units of the cleaning unit 100 are arranged on the patient table 17. In addition, individual parts and/or units of the cleaning unit 100 are also arranged on the patient support apparatus 16, e.g. on a base unit 27 of the patient support apparatus 16. In this regard, the cleaning unit 100 includes at least one unit that is arranged and/or integrated within the patient table 17. In other words, in this case, the at least one unit is arranged within an area enclosed by a housing of the patient table 17.

The cleaning unit 100 comprises a spray unit (also referred to herein as a sprayer) 101 embodied to dispense a cleaning agent. In this case, the spray unit 101 comprises at least one nozzle 102 embodied to dispense the cleaning agent, e.g. to spray a cleaning fluid. In this case, the spray unit 101 may comprise two or more nozzles 102 so that targeted distribution of the cleaning agent, e.g. targeted spraying of the cleaning fluid, onto the enclosure 14 surrounding the patient receiving area 12 can be provided. In this case, the at least one unit of the cleaning unit 100 arranged within the patient table 17 includes the at least one nozzle 102 of the spray unit 101. The at least one nozzle 102 of the spray unit 101 is arranged in a front area 28 of the patient table 17. The front area 28 is arranged in a front area in the entry direction 29 of the patient table 17 in which the patient table 17 is moved into the patient receiving area 12.

In addition, the spray unit 101 comprises a storage tank 103. The storage tank 103 is embodied to receive the cleaning agent. The storage tank 103 is arranged on the base unit 27 of the patient support apparatus 16. In this regard, the storage tank 103 is arranged on the base unit 27 in such a way that it can be reached by operators, e.g. medical cleaning staff, to replace the storage tank 103 and/or to refill the storage tank 103. In this regard, the base unit 27 can include a compartment accessible from the outside for receiving the storage tank 103.

In addition, the cleaning unit 100, e.g. the spray unit 101, comprises a cleaning agent duct 104 and/or a cleaning agent line, wherein the cleaning agent duct 104 and/or the cleaning agent line is arranged within the patient support apparatus 16 for transporting cleaning agent between the storage tank 103 and the at least one nozzle 102. The cleaning agent duct 104 and/or the cleaning agent line can, for example, comprise a hose and/or further supply lines that appear advisable to the person skilled in the art. In addition, the cleaning unit 100, e.g. the spray unit 101, comprises a pump 105 for transporting and/or conveying the cleaning agent within the cleaning agent duct 104 and/or within the cleaning agent line. The pump 105 is likewise arranged within the base unit 27 of the patient support apparatus 16.

In this regard, the cleaning unit 100, e.g. the spray unit 101, is activated for a cleaning operation while the patient table 17 is moved into the patient receiving area 12 so that the patient receiving area 12, e.g. the enclosure 14 surrounding the patient receiving area 12, is sprayed with cleaning agent along the entire length of the patient receiving area 12.

FIG. 2 illustrates a representation of an alternative exemplary embodiment of a cleaning unit 200. Components, features, and functions that are substantially the same are basically given the same reference numbers. The following description is substantially restricted to the differences from the exemplary embodiment in FIG. 1, wherein reference is made to the description of the exemplary embodiment in FIG. 1 with respect to components, features and functions that remain the same.

The cleaning unit 200 in FIG. 2 is likewise embodied for cleaning the enclosure 14 surrounding the patient receiving area 12 and is arranged at least partially on the patient table 17. In this case, the cleaning unit 200 comprises a spray unit 201 with at least one nozzle 202, a storage tank 203, a cleaning agent duct 204, and a pump 205. Reference is made to the statements relating to FIG. 1 with respect to the arrangement and embodiment of the spray unit 201.

The cleaning unit 200 further comprises a drying unit (also referred to herein as a dryer) 206. The drying unit 206 is embodied to allow drying air to flow into the patient receiving area 12. In the present exemplary embodiment, the drying unit 206 is at least partially arranged within the patient table 17. For instance, in this case the drying unit 206 comprises at least one air nozzle 207 arranged within the patient table 17. The drying unit 206 further comprises a ventilation duct 208 and a fan 209 and/or ventilator. The ventilator and/or fan 209 is embodied to generate an air flow. In addition, the fan 209 and/or ventilator are arranged within the base unit 27. The ventilation duct 208 is embodied to supply air into the patient receiving area 12, e.g. from the fan 209 and/or ventilator to the at least one air nozzle 207. In addition, the drying unit 206 can also comprise an air aspiration opening (not shown in further detail) arranged on an outer side of the base unit 27.

In this case, the spray unit 201 of the cleaning unit 200 can be activated for a cleaning operation while the patient table 17 is moved into the patient receiving area 12 so that the patient receiving area 12, e.g. the enclosure 14 surrounding the patient receiving area 12, is sprayed with cleaning agent along the entire length of the patient receiving area 12. On the other hand, when the patient table 17 is moved out of the patient receiving area 12, the drying unit 206 of the cleaning unit 200 can be activated and in this way the patient receiving area 12, e.g. the enclosure 14 surrounding the patient receiving area 12, can be dried.

In an alternative embodiment of the drying unit 206, the at least one air nozzle 207 can also be embodied in one piece and/or in one part with the at least one nozzle 202 of the suction unit 201. In this case, in a first mode of operation, the at least one nozzle 202, 207 could distribute the cleaning agent and, in a second mode of operation, introduce an air flow into the patient receiving area 12. In a further alternative embodiment of the drying unit 206, the at least one air nozzle 207 can also be arranged in the enclosure 14 surrounding the patient receiving area 12. In such an embodiment of the drying unit 206, the enclosure 14 comprises a ventilation opening through which drying air can flow into the patient receiving area 12. In a further alternative embodiment of the drying unit 206, this unit can also be embodied in one part and/or in one piece with a patient ventilation unit (not shown in further detail). The patient ventilation unit may comprise a ventilation opening, arranged in the enclosure 14 surrounding the patient receiving area 12.

FIG. 3 illustrates a representation of an alternative exemplary embodiment of a cleaning unit 300. Components, features and functions that are substantially the same are basically given the same reference numbers. The following description is substantially restricted to the differences from the exemplary embodiments in FIGS. 1 and 2, wherein reference is made to the description of the exemplary embodiments in FIGS. 1 and 2 with respect to components, features and functions that remain the same.

The cleaning unit 300 in FIG. 3 is likewise embodied for cleaning the enclosure 14 surrounding the patient receiving area 12 and is at least partially arranged on the patient table 17. In this case, the cleaning unit 300 comprises a spray unit 301 with at least one nozzle 302, a storage tank 303, a cleaning agent duct 304, and a pump 305. Reference is made to the statements relating to FIGS. 1 and 2 with respect to the arrangement and embodiment of the spray unit 301.

In addition, the cleaning unit 300 comprises a drying unit 306, wherein, in the present exemplary embodiment, the drying unit 306 is arranged by way of example on the enclosure 14 surrounding the patient receiving area 12. In this case, the drying unit 306 comprises an air nozzle 307, a ventilation duct 308, and a fan 309 and/or ventilator arranged within a housing surrounding the scanner unit 11. A mode of operation of the drying unit 306 is substantially the same as the mode of operation of the drying unit 206 in FIG. 2. Alternatively, the drying unit 306 could also be embodied as described in FIG. 2.

The cleaning unit 300 further comprises a suction extraction unit (also referred to herein as an extractor) 310. The suction extraction unit 310 can extract a cleaning agent aerosol by suction after the cleaning agent has been dispensed from the patient receiving area 12. In the present exemplary embodiment, the suction extraction unit 310 is at least partially arranged on the patient table 17. For this purpose, the suction extraction unit 310 comprises at least one suction nozzle 311 arranged on the patient table 17. The at least one suction nozzle 311 is arranged in the direction of a longitudinal extension of the patient table 17 downstream of the nozzle 302 of the suction unit 301. The suction extraction unit 310 furthermore includes a fan 312 and/or ventilator and/or a suction extraction pump for generating an air flow, e.g. a suction flow that effects the extraction by suction of air and/or cleaning agent aerosols from the patient receiving area 12. In addition, the suction extraction unit 310 includes a suction extraction duct 313 for discharging the aspirated air and/or cleaning agent aerosols from the patient receiving area 12 from the at least one suction nozzle 311 to a blow-out opening 314 of the suction extraction unit 310. The blow-out opening 314 is arranged on a housing of the base unit 27 of the patient support apparatus 16. In addition, the fan 312 and/or ventilator and/or the suction extraction pump is arranged within the suction extraction duct 313. The suction extraction unit 310 further comprises a filter 315 designed to clean the aspirated air with the cleaning agent aerosols. The filter 315 is arranged within the suction extraction duct 313, wherein the filter 315 is arranged in the area of the blow-out opening 314 within the suction extraction duct 313.

In an alternative embodiment of the cleaning unit 200, e.g. the suction extraction unit 310, the unit can also be at least partially embodied in one piece and/or in one part with the spray unit 301. In this case, e.g. the at least one suction nozzle 311 of the suction extraction unit 310 can be embodied in one piece and/or in one part with the nozzle 302 of the spray unit 301. In this regard, the at least one nozzle 302 can include a type of double nozzle embodied both to distribute the cleaning agent, e.g. to spray the cleaning fluid, and to extract cleaning agent aerosols by suction.

In this case, for a cleaning operation, the spray unit 301 of the cleaning unit 300 can be activated while the patient table 17 is moved into the patient receiving area 12, so that the patient receiving area 12, e.g. the enclosure 14 surrounding the patient receiving area 12, is sprayed with cleaning agent along the entire length of the patient receiving area 12. In this regard, the suction extraction unit 310 can be activated at the same time as the patient table 17 is moved into the patient receiving area 12 or also only activated to extract cleaning agent aerosols from the patient receiving area 12 by suction when the patient table 17 is moved out of the patient receiving area 12. In addition, the drying unit 306 of the cleaning unit 300 can be activated while the patient table 17 is moved out of the patient receiving area 12 and in this way the patient receiving area 12, e.g. the enclosure 14 surrounding the patient receiving area 12, can be dried.

FIG. 4 illustrates a representation of an alternative exemplary embodiment of a cleaning unit 400. Components, features and functions that are substantially the same are basically given the same reference numbers. The following description is substantially restricted to the differences from the exemplary embodiments in FIGS. 1 to 3, wherein reference is made to the description of the exemplary embodiments in FIGS. 1 to 3 with respect to components, features and functions that remain the same.

The cleaning unit 400 in FIG. 4 is likewise embodied for cleaning the enclosure 14 surrounding the patient receiving area 12 and is arranged at least partially on the patient table 17. In this case, the cleaning unit 400 comprises a spray unit 401 with at least one nozzle 402, a storage tank 403, a cleaning agent duct 404 and a pump 405. In this case, reference is made to the statements relating to FIGS. 1 to 3 with respect to the arrangement and embodiment of the spray unit 401.

In addition, the cleaning unit 400 in FIG. 4 also comprises a drying unit 406 arranged at least partially within the patient table 17. The drying unit 406 comprises an air nozzle 407, a ventilation duct 408, and a fan 409 and/or ventilator. Reference is made to the statements relating to FIG. 2 with respect to the arrangement and embodiment of the drying unit 406.

The cleaning unit 400 further comprises a suction extraction unit 410 by means of which a cleaning agent aerosol can be extracted from the patient receiving area 12 by suction after the cleaning agent has been dispensed. The suction extraction unit 410 is at least partially arranged on the enclosure 14 surrounding the patient receiving area 12. The suction extraction unit 410 comprises at least one suction nozzle 411 arranged on the enclosure 14 surrounding the patient receiving area 12. In addition, the suction extraction unit 410 comprises a fan 412 and/or ventilator and/or a suction extraction pump, a suction extraction duct 413, a blow-out opening 414, and a filter 415. The blow-out opening 414 is arranged on a housing of the scanner unit 11, e.g. on a rear side of the scanner unit 11. The suction extraction duct 413 is arranged within an area surrounded by the housing of the scanner unit 11 and embodied to transport air and/or cleaning agent aerosols extracted by suction from the patient receiving area 12 to the blow-out opening 414. Reference is made to the statement relating to FIG. 3 with respect to the mode of operation of the suction extraction unit 410.

In this case, for a cleaning operation, the spray unit 401 of the cleaning unit 400 can be activated while the patient table 17 is moved into the patient receiving area 12 so that the patient receiving area 12, e.g. the enclosure 14 surrounding the patient receiving area 12, is sprayed with the cleaning agent along the entire length of the patient receiving area 12. In this regard, the suction extraction unit 410 can be activated to extract cleaning agent aerosols from the patient receiving area 12 by suction at the same time as the patient table 17 is moved into the patient receiving area 12 or also only when the patient table 17 is moved out of the patient receiving area 12. In addition, the drying unit 406 of the cleaning unit 400 can be activated while the patient table 17 is moved out of the patient receiving area 12 and in this way the enclosure 14 surrounding the patient receiving area 12 can be dried.

FIG. 5 is a representation of an alternative exemplary embodiment of a cleaning unit 500. Components, features, and functions that are substantially the same are basically given the same reference numbers. The following description is substantially restricted to the differences from the exemplary embodiments in FIGS. 1 to 4, wherein reference is made to the description of the exemplary embodiments in FIGS. 1 to 4 with respect to components, features and functions that remain the same.

The cleaning unit 500 in FIG. 5 is likewise embodied for cleaning the enclosure 14 surrounding the patient receiving area 12 and is at least partially arranged on the patient table 17. In the present exemplary embodiment, the cleaning unit 500 is at least partially embodied as an additional unit, wherein the additional unit can be arranged and/or positioned on the patient table 17 for cleaning the enclosure 14 surrounding the patient receiving area 12. In this case, the cleaning unit 500 comprises a spray unit 501 which is included in the additional unit. In this regard, the spray unit 501 includes at least one nozzle 502 embodied to distribute the cleaning agent, e.g. to spray a cleaning fluid. The spray unit 501 furthermore comprises a storage tank 503, a cleaning agent duct 504, and a pump 505, which are likewise included in the additional unit. The additional unit, e.g. the spray unit 501, is positioned and/or arranged on the patient table 17 to clean the enclosure 14 surrounding the patient receiving area 12 such that the at least one nozzle 502 of the spray unit 501 is arranged in the front area 28 of the patient table 17. Reference is made to the statements relating to FIGS. 1 to 4 with respect to the mode of operation of the spray unit 501.

The cleaning unit 500 further comprises a drying unit 506, which is likewise included in the additional unit and can be arranged and/or positioned on the patient table 17. In this regard, the drying unit 506 comprises at least one air nozzle 507, a ventilation duct 508 and a fan 509 and/or ventilator. Reference is made to the statements relating to FIG. 3 with respect to the arrangement and embodiment of the drying unit 506.

The cleaning unit 500 further comprises a suction extraction unit 510, which is likewise included by the additional unit that can be arranged and/or positioned on the patient table 17. The suction extraction unit 510 likewise comprises at least one suction nozzle 511, a fan 512, and/or ventilator and/or a suction extraction pump, a suction extraction duct 513, a blow-out opening 514, and a filter 515, which are likewise included in the additional unit. Reference is made to the statements relating to FIGS. 3 to 4 with respect to the mode of operation of the suction extraction unit 510.

To clean the enclosure 14 surrounding the patient receiving area 12, the additional unit of the cleaning unit 500 is first positioned on the patient table 17. In this case, for a cleaning operation, the spray unit 501 of the cleaning unit 500 can be activated while the patient table 17 is moved into the patient receiving area 12 so that the patient receiving area 12, e.g. the enclosure 14 surrounding the patient receiving area 12, is sprayed with the cleaning agent along the entire length of the patient receiving area 12. In this regard, the suction extraction unit 510 can be activated to extract cleaning agent aerosols from the patient receiving area 12 by suction at the same time as the patient table 17 is moved into the patient receiving area 12 or also only when the patient table 17 is moved out of the patient receiving area 12. In addition, the drying unit 506 of the cleaning unit 500 is activated while the patient table 17 is moved out of the patient receiving area 12 and in this way the patient receiving area 12, e.g. the enclosure 14 surrounding the patient receiving area 12 is dried.

The magnetic resonance apparatuses 10 represented in FIGS. 1 to 5 can obviously include further components usually comprised by magnetic resonance apparatuses 10. In addition, the general mode of operation of a magnetic resonance apparatus 10 is known to the person skilled in the art so that no more detailed description of further components will be given.

FIG. 6 is a representation of a method for cleaning the patient receiving area 12, e.g. the enclosure 14 surrounding the patient receiving area 12, of the magnetic resonance apparatus 10 by means of one of the cleaning units 200, 300, 400, 500 represented in FIGS. 2 to 5. If the method is executed with a cleaning unit 500 which is at least partially embodied as an additional unit, the additional unit is positioned and/or arranged on the patient table 17 of the patient support apparatus 16 by a user, e.g. a medical operator and/or a member of the cleaning staff, before starting the method for cleaning the enclosure 14 surrounding the patient receiving area 12. In this regard, the user positions and/or arranges the additional unit on the patient table 17 in such a way that the spray unit 501, e.g. the at least one nozzle 502 of the spray unit 501, is arranged in the front area 28 of the patient table 17.

If the cleaning unit 200, 300, 400 is embodied in accordance with FIGS. 2 to 4, the cleaning unit 200, 300, 400 is already at least partially integrated in the patient table 17 so that no further preparations are necessary in order to execute the method for cleaning the patient receiving area 12.

At the start, the user starts the method for cleaning the patient receiving area 12. This can, for example, take place by means of the input unit 26 of the user interface 24 and/or an operating unit (not shown in further detail) of the cleaning unit 200, 300, 400, 500. In a first method step 600, the patient table 17 is moved into the patient receiving area 12. At the same time as the patient table 17 is moved into the patient receiving area 12, in a second method step 601, a first cleaning step of a cleaning operation takes place. In this regard, the first cleaning step includes dispensing and/or distributing a cleaning agent by means of the cleaning unit 200, 300, 400, 500. For instance, the first cleaning step includes spraying a cleaning fluid by means of the spray unit 201, 301, 401, 501 of the cleaning unit 200, 300, 400, 500.

A third method step 602 includes a second cleaning step of the cleaning operation, wherein the second cleaning step includes a drying step and/or a suction extraction step. The drying step is executed by means of the drying unit 206, 306, 406, 506 of the cleaning unit 200, 300, 400, 500. The suction extraction step is executed by means of the suction extraction unit 310, 410, 510 of the cleaning unit 300, 400, 500.

In this regard, the third method step 602, e.g. the second cleaning step of the cleaning operation, can likewise be executed while the patient table 17 is moved into the patient receiving area 12, e.g. if the second cleaning step includes the suction extraction step. In addition, the third method step 602, e.g. the second cleaning step of the cleaning operation, can also be executed while the patient table 17 is moved out of the patient receiving area 12, e.g. if the second cleaning step includes the drying step and/or the suction extraction step.

Preferably, the method for cleaning the patient receiving area 12, e.g. the enclosure 14 surrounding the patient receiving area 12, proceeds automatically and/or autonomously after being started once by a user. For this purpose, the cleaning unit 100, 200, 300, 400, 500 comprises a computing unit, which controls the course of the method for cleaning the enclosure 14 surrounding the patient receiving area 12. In the present, the computing unit of the cleaning unit 100, 200, 300, 400, 500 is integrated within the system control unit 23 of the magnetic resonance apparatus 10. In addition, the computing unit of the cleaning unit can also be embodied separately from the system control unit 23.

To execute the method for cleaning the patient receiving area 12, the computing unit of the cleaning unit 100, 200, 300, 400, 500 comprises at least one computing module and/or processor. For example, the computing unit is e.g. embodied to execute computer-readable instructions to execute the method according to the disclosure for cleaning the patient receiving area 12. For example, the computing unit includes a storage unit, wherein computer-readable information is stored on the storage unit, wherein the computing unit is embodied to load the computer-readable information from the storage unit and to execute the computer-readable information in order to execute a method according to the disclosure for cleaning the patient receiving area 12.

The components of the computing unit can be predominately embodied in the form of software components. However, in principle, these components can also to some extent, in particular where particularly fast calculations are involved, be implemented in the form of software-supported hardware components, for example FPGAs or the like. The required interfaces can, for example if this only involves a transfer of data from other software components, be embodied as software interfaces. However, they can also be embodied as hardware interfaces actuated by means of suitable software. It is obviously also conceivable for several of the components named to be implemented in combination in the form of an individual software component or software-supported hardware-component.

Although the disclosure has been illustrated and described in more detail by the preferred exemplary embodiments, the disclosure is not restricted by the disclosed examples and other variations can be derived herefrom by the person skilled in the art without departing from the scope of protection of the disclosure.

The various components described herein may be referred to as "units." Such components may be implemented via any suitable combination of parts, components, hardware, and/or software components as applicable and/or known to achieve the intended functionality of the respective units. This may include mechanical and/or electrical components, FPGAs, processors, processing circuitry, or other suitable hardware components configured to execute instructions or computer programs that are stored on a suitable computer readable medium. Regardless of the particular implementation, such units when applicable and relevant may alternatively be referred to herein as "circuitry," "processors," or "processing circuitry".

What is claimed is:

1. A magnetic resonance imager, comprising:
a scanner; and
a patient receiving area at least partially surrounded by the scanner, wherein the scanner comprises:
an enclosure at least partially surrounding the patient receiving area;
a patient support with a patient table that is configured to move horizontally within the patient receiving area; and
a cleaner, comprising:
a sprayer including one or more cleaning agent nozzles that are coupled to the patient table, the one or more cleaning agent nozzles forming part of a dedicated cleaning agent distribution system,
wherein the sprayer is configured to spray, via a distribution of a cleaning agent via the one or more cleaning agent nozzles, the enclosure at least partially surrounding the patient receiving area with the cleaning agent, and
wherein the cleaner is activated for a cleaning operation upon movement of the patient table such that the sprayer sprays the enclosure with the cleaning agent while the patient table is moving into the patient receiving area; and
a dryer including one or more air nozzles that are separate from the one or more cleaning agent nozzles, the one or more air nozzles forming part of a dedicated air distribution system,
wherein the dryer is configured to supply air into the patient receiving area to dry the enclosure after being sprayed with the cleaning agent.

2. The magnetic resonance imager as claimed in claim 1, wherein the one or more cleaning agent nozzles are arranged in a front area of the patient table with respect to an entry direction of the patient table when moved into the patient receiving area.

3. The magnetic resonance imager as claimed in claim 1, wherein the sprayer comprises a storage tank arranged on a base of the patient support.

4. The magnetic resonance imager as claimed in claim 1, wherein the dryer is at least partially arranged on the patient table and/or on the enclosure surrounding the patient receiving area.

5. The magnetic resonance imager as claimed in claim 1, wherein the cleaner comprises an extractor.

6. The magnetic resonance imager as claimed in claim 5, wherein the extractor is at least partially arranged on the enclosure surrounding the patient receiving area and/or on the patient table.

7. The magnetic resonance imager as claimed in claim 5, wherein the extractor includes at least one suction extraction duct with a filter.

8. The magnetic resonance imager as claimed in claim 1, wherein the cleaner is activated to execute the cleaning operation upon movement of the patient table such that, while the patient table is moving into the patient receiving area, the sprayer sprays the enclosure with the cleaning agent along an entire length of the patient receiving area.

9. The magnetic resonance imager as claimed in claim 1, wherein the dryer is configured to perform a drying operation as the patient table is moving out of the patient receiving area.

10. The magnetic resonance imager as claimed in claim 1, wherein the cleaner is activated to perform a further cleaning operation upon subsequent movement of the patient table such that, while the patient table is moving out of the patient receiving area, the sprayer sprays the enclosure with the cleaning agent along the entire length of the patient receiving area.

11. The magnetic resonance imager as claimed in claim 3, wherein the base of the patient support comprises a compartment accessible from an outside of the base, and
wherein the compartment is configured to receive the storage tank.

12. The magnetic resonance imager as claimed in claim 11, wherein the cleaner comprises a cleaning agent line arranged within the patient support, and
wherein the cleaning agent line is configured to transport the cleaning agent from the storage tank to the sprayer.

13. The magnetic resonance imager as claimed in claim 12, wherein the cleaner comprises a pump configured to transport the cleaning agent within the cleaning agent line, and
wherein the pump is arranged within the base of the patient support.

14. The magnetic resonance imager as claimed in claim 1, wherein an entirety of the cleaner is arranged within and/or on the patient table.

15. The magnetic resonance imager of claim 1, wherein the one or more cleaning agent nozzles only distribute the cleaning agent, and
wherein the one or more air nozzles only supply the air.

16. The magnetic resonance imager of claim 1, wherein the cleaner further comprises a controller configured to execute computer-readable instructions to cause (i) the sprayer to spray the enclosure at least partially surrounding the patient receiving area with the cleaning agent, and (ii) the dryer to supply air into the patient receiving area to dry the enclosure after being sprayed with the cleaning agent.

17. The magnetic resonance imager of claim 1, wherein the dedicated cleaning agent distribution system comprises a dedicated set of cleaning agent ducts coupled to the one or more cleaning agent nozzles and to a cleaning agent storage tank, and wherein the dedicated air distribution system comprises a dedicated set of air supply ducts coupled to the one or more air nozzles and to a fan and/or ventilator.

\* \* \* \* \*